United States Patent
Finn et al.

(10) Patent No.: US 11,096,812 B2
(45) Date of Patent: Aug. 24, 2021

(54) DELIVERY SYSTEM AND METHOD FOR LOADING A SELF-EXPANDING COLLAPSIBLE HEART VALVE

(71) Applicant: St. Jude Medical, Cardiology Division, Inc., St. Paul, MN (US)

(72) Inventors: Ryan Finn, Roseville, MN (US); Keith High, White Bear Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 226 days.

(21) Appl. No.: 16/232,554

(22) Filed: Dec. 26, 2018

(65) Prior Publication Data

US 2019/0224028 A1    Jul. 25, 2019

Related U.S. Application Data (60) Provisional application No. 62/620,010, filed on Jan. 22, 2018.

(51) Int. Cl.
| | |
|---|---|
| *A61F 2/95* | (2013.01) |
| *A61F 2/97* | (2013.01) |
| *A61F 2/24* | (2006.01) |

(52) U.S. Cl.
CPC .......... *A61F 2/9525* (2020.05); *A61F 2/2427* (2013.01); *A61F 2/97* (2013.01); *A61F 2/2418* (2013.01); *A61F 2/9522* (2020.05)

(58) Field of Classification Search
CPC ........ A61F 2/97; A61F 2/2427; A61F 2/2522; A61F 2/9522; A61F 2/9525; A61F 2/9524; A61F 2/9526
See application file for complete search history.

(56) References Cited

U.S. PATENT DOCUMENTS

| | | | | |
|---|---|---|---|---|
| 6,149,680 | A | * 11/2000 | Shelso | A61F 2/95 623/1.11 |
| 2010/0057185 | A1 | * 3/2010 | Melsheimer | A61F 2/95 623/1.12 |
| 2010/0262157 | A1 | * 10/2010 | Silver | A61F 2/95 606/108 |
| 2010/0292779 | A1 | * 11/2010 | Straubinger | A61F 2/2427 623/1.23 |
| 2017/0000634 | A1 | * 1/2017 | Helmick | A61F 2/95 |
| 2017/0003557 | A1 | 1/2017 | Lee et al. | |

FOREIGN PATENT DOCUMENTS

WO    2009091509 A1    7/2009

\* cited by examiner

*Primary Examiner* — Sarah A Simpson
(74) *Attorney, Agent, or Firm* — Lerner, David, Littenberg, Krumholz & Mentlik, LLP (57) ABSTRACT

A delivery system has a delivery capsule with a detachable portion including first and second open ends with a tapered wall extending therebetween to compress and guide a collapsible heart valve into the delivery capsule. The detachable portion may be detached from the delivery capsule after loading the collapsible heart valve to leave a smooth distal surface on the delivery capsule. Detachment of the detachable portion may occur by breaking or removing a frangible member interposed between the detachable portion and the delivery capsule.

13 Claims, 9 Drawing Sheets

DELIVERY SYSTEM AND METHOD FOR LOADING A SELF-EXPANDING COLLAPSIBLE HEART VALVE

CROSS-REFERENCE TO RELATED APPLICATIONS

The present application claims the benefit of the filing date of U.S. Provisional Patent Application No. 62/620,010, filed Jan. 22, 2018, the disclosure of which is hereby incorporated herein by reference.

BACKGROUND OF THE INVENTION

The present disclosure relates to prosthetic heart valve implantation and, more particularly, to delivery systems and methods for loading a self-expanding collapsible heart valve into the same.

Prosthetic heart valves may be formed from biological materials such as harvested bovine valves or pericardium tissue. Such valves are typically fitted within a stent, which may be inserted into the heart at the annulus of the compromised native valve to replace the native valve. To perform such insertion procedure, it is often necessary to compress the stent to a reduced diameter for loading into the delivery device.

In the case of valves formed from biological materials, the stented valve is preferably preserved in the open condition for storage as compression of the valve material for extended periods compromises the integrity of the biological valve. It is therefore necessary to crimp the valve, or reduce its diameter for loading in the delivery device, in the operating arena.

Excessive crimping of valves for loading, i.e., compressing valves to more than the recommended limit, may compromise the integrity of the valve and/or the delivery system. This is particularly relevant for valves that include layers extending outside the stent body to prevent fluid flow around the valve after implantation. The extended portions may get entangled with the delivery system during loading, leading to excessive crimping of these valves. Furthermore, an operator loading these valves will need to exert additional loading force to push the entangled valve through the delivery system to complete the loading.

Present crimping devices and methods for collapsing a stented valve, including direct radial assemblies, may be particularly challenging to use for valves with layers extending outside the stent body as they are difficult to master, are time consuming, impart undue stress on the stented valve, or exhibit other undesirable qualities. It would therefore be beneficial to provide a delivery system and a method for loading a self-expanding collapsible heart valve into the delivery system that overcome these deficiencies.

BRIEF SUMMARY OF THE INVENTION

Disclosed herein are delivery systems for a collapsible heart valve and methods for loading the heart valve to the same.

In a first aspect of the present invention, a delivery system is provided. The delivery system may include a delivery capsule and a detachable portion. The delivery capsule may have a longitudinal axis and a distal opening to receive a collapsible heart valve. The distal opening may have an internal diameter. The detachable portion may have a first open end with a first diameter, a second open end with a second diameter, and a guide wall. The guide wall may define an open space adapted to receive the valve. The first open end may be attached to the distal opening of the delivery capsule. The first diameter may be substantially the same as the internal diameter of the distal opening of the delivery capsule such that inner surfaces of the guide wall and the distal opening may form a continuous surface extending from the detachable portion and into the delivery capsule. The detachable portion may be detachable from the delivery capsule.

In accordance with the first aspect, the second open end may have a second diameter greater than the first diameter. The guide wall may decrease in diameter from the second open end to the first open end. The first diameter may be less than a diameter of the collapsible heart valve in an uncompressed state such that the heart valve may be compressed as it passes from the second open end to the first open end. The guide wall may include one or more walls. The guide wall may include one or more struts.

Further in accordance with the first aspect, the detachable portion may be attached to the delivery capsule by a frangible member such that the detachable portion may be detached from the delivery capsule by breaking the frangible member. The frangible member may include a breakaway band such that the detachable portion may be detached from the delivery capsule by breaking the breakaway band. The frangible member may be formed by a procedure selected from the group consisting of creasing, crimping, embossing, perforating and scoring the detachable portion. The frangible member may be a marker to position and guide the collapsible heart valve. The detachable portion may be made of a flexible material. The flexible material may be polytetrafluoroethylene. The detachable portion may be connected to the delivery capsule by releasable connectors that enable the detachable portion to be detached from and reattached to the delivery capsule.

Still further in accordance with this first aspect, the delivery system may include a support structure. The support structure may be configured to be placed around the delivery capsule and the detachable portion. A distal portion of the support structure may be similar in shape to the guide wall.

A second aspect of the present invention is a method of loading a collapsible heart valve into a delivery system. A method in accordance with this aspect of the invention may include the steps of providing a delivery system with an integrated detachable portion and a retaining element, extending a retaining element of the delivery system, attaching a heart valve to the retaining element, and loading the heart valve into the delivery system. The delivery system may have delivery capsule with a distal opening. The distal opening may have an internal diameter. The detachable portion may have a first open end with a first diameter, a second open end with a second diameter greater than the first diameter, and a tapered wall decreasing in diameter from the second open end to the first open end. The tapered wall may define an open space. The first open end may be integrally connected to the distal opening of the delivery capsule. The first diameter may be substantially the same as the internal diameter of the distal opening of the delivery capsule such that inner surfaces of the tapered wall and the distal opening may form a continuous surface extending from the detachable portion and into the delivery capsule. The retaining element may be extended distally away from the distal opening. The heart valve may be attached to the retaining element. The heart valve may be loaded into the delivery capsule by retracting the retaining element proximally such that the tapered wall collapses the heart valve as the heart valve moves from the second open end to the first open end and into the delivery capsule.

In accordance with the second aspect, the method may include the step of removing the detachable portion from the delivery system. The detachable portion may be removed from the delivery system such that the distal opening may have a smooth distal surface. The step of removing the detachable portion may include the step of breaking a frangible member between the detachable portion and the delivery capsule. The step of removing the detachable portion may include the step of peeling away a band between the detachable portion and the delivery capsule. The step of removing the detachable portion may include the step of cutting the detachable portion from the delivery capsule.

Further in accordance with the second aspect, the loading step may include placing a support structure around the delivery capsule and the detachable portion prior to retracting the retaining element proximally such that the support structure may guide the heart valve as the heart valve moves from the second opening to the first opening and into the delivery capsule.

BRIEF DESCRIPTION OF THE DRAWINGS

A more complete appreciation of the subject matter of the present invention and the various advantages thereof may be realized by reference to the following detailed description, in which reference is made to the following accompanying drawings.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention. As used herein, the term "proximal" refers to the end of the loading assembly, or portion thereof, which is closest to the operator in use, while the term "distal" refers to the end of the loading assembly, or portion thereof, which is farthest from the operator in use.

Figure 1:
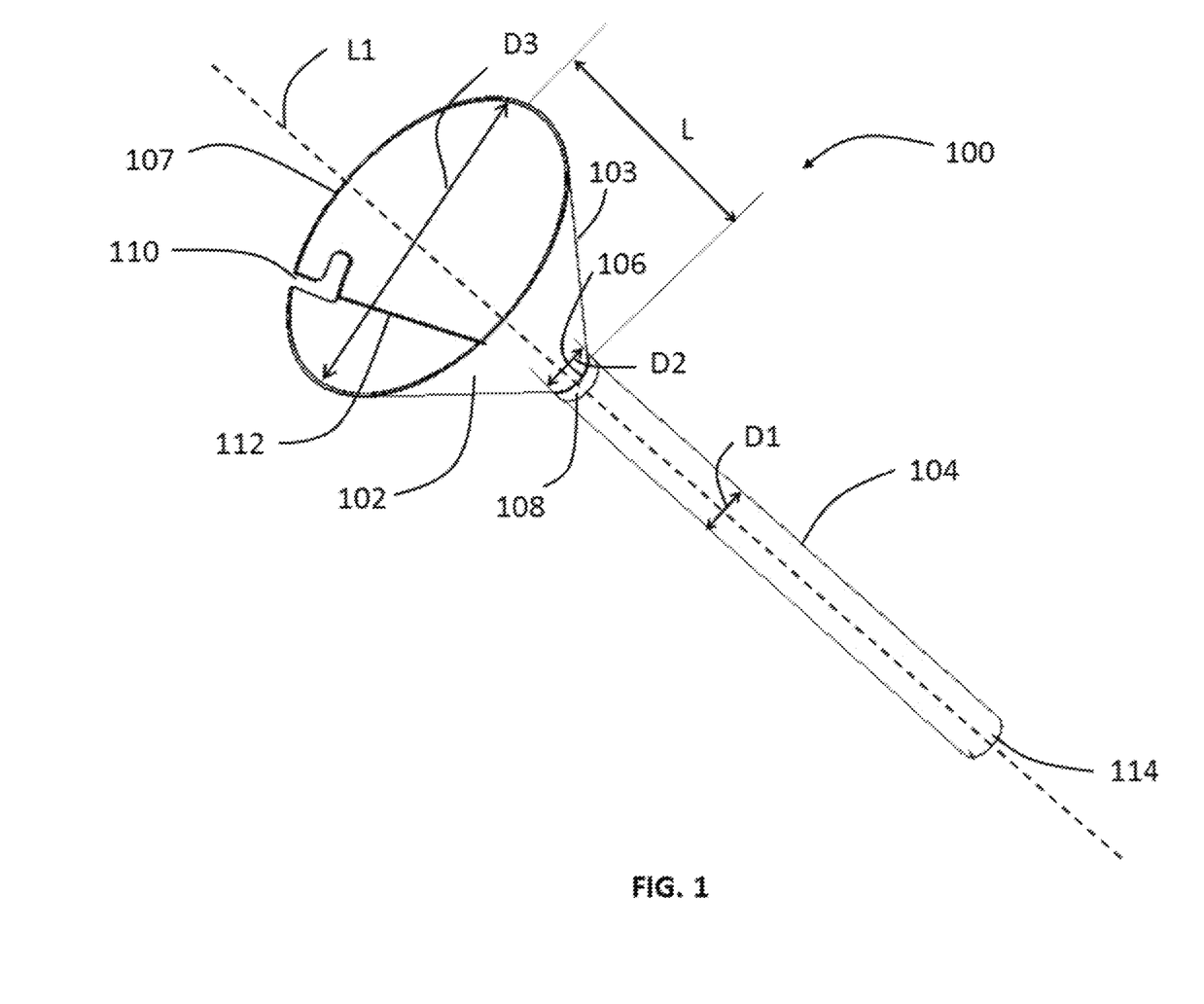
FIG. 1 is a perspective view of the distal portion of a delivery system with a detachable portion according to a first embodiment of the present invention.
Figure 2:
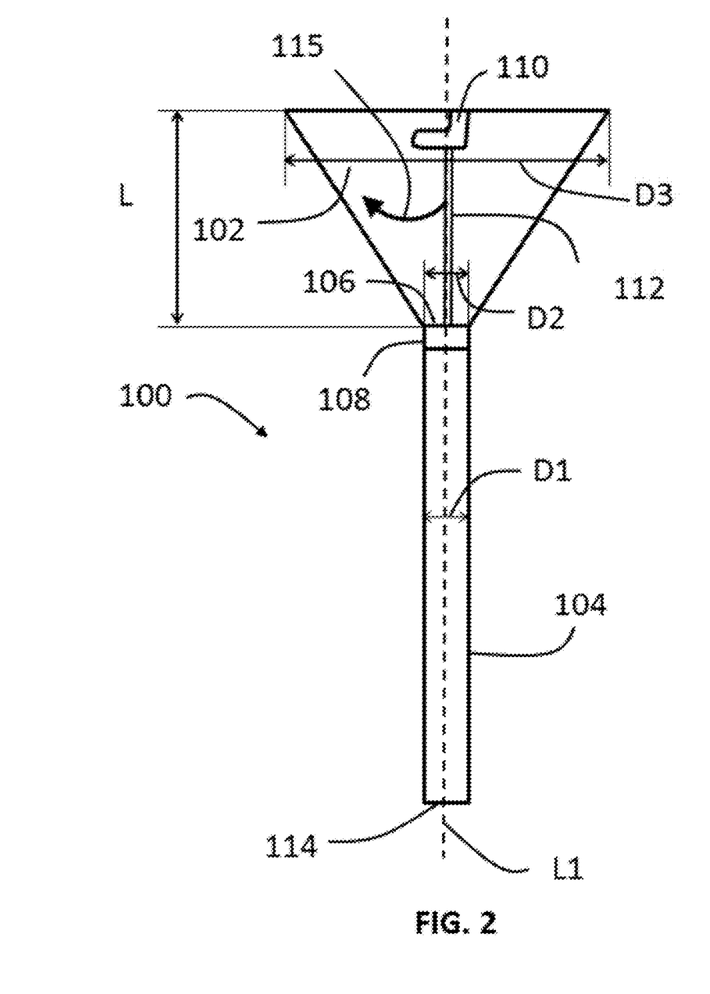
FIG. 2 is a front view of the distal portion of the delivery system of FIG. 1.

The present disclosure relates to systems and methods for loading a self-expanding collapsible heart valve, stent or other similar implant into a delivery system. A distal portion of an exemplary delivery system 100 is shown in FIGS. 1 and 2. Delivery system 100 includes a sheath or delivery capsule 104 extending along a longitudinal axis L1 and having an internal diameter D1. As more fully explained below, delivery system 100 as shown in FIGS. 1 and 2 includes other components that are retracted within sheath 104. The proximal end 114 of sheath 104 is connected to a handle 124 (FIG. 5) which is used, inter alia, to control extension and retraction of components housed in sheath 104. The distal end of sheath 104 includes a band 108. Band 108 is a protective layer that provides a smooth distal edge without rough or sharp edges when a detachable portion 102 is removed from sheath 104. This allows safe advancement of delivery system 100 to a target site within a patient. Band 108 may also function as a marker that facilitates precise insertion and positioning of delivery system 100 during an implantation procedure.

Detachable portion 102 is generally in the shape of a cone that extends symmetrically about longitudinal axis L1, with a first opening 106 at its proximal end and a second opening 107 at its distal end. First opening 106 has a diameter D2 that is the same or substantially the same as the internal diameter D1 of sheath 104, as best shown in FIG. 2. When first opening 106 is aligned with longitudinal axis L1 and attached to band 108, a smooth continuous internal passage is formed to facilitate passage of a compressible implant from detachable device 102 to sheath 104. Second opening 107 has a diameter D3 that is larger than diameter D2 to receive the compressible implant in an expanded condition. A wall 103 tapers inwardly from second opening 107 to first opening 106 to guide the compressible implant as it passes through detachable portion 102. A length L defines the distance between first opening 106 and second opening 107. As more fully explained below, varying the dimensions D3 and L of detachable portion 102 will vary the compression levels and compression rates imparted to the compressible implant as it passes through detachable portion 102. Where dimension D2 cannot be varied, varying dimension D3 while maintaining length L constant or varying length L while maintaining diameter D3 constant will vary the rate of compression of the compressible implant as it passes through the detachable portion 102.

Detachable portion 102 may be formed integrally with the band 108 of sheath 104, and may include various features to enable it to be conveniently detached therefrom. As shown in FIGS. 1 and 2, detachable portion 102 includes a frangible seam 112 extending from first opening 106 to second opening 107. Detachable portion 102 may be creased, crimped, embossed, perforated, scored or otherwise weakened along seam 112 so that an operator may conveniently pull apart detachable portion 102 at the seam. An L-shaped slot 110 with a pull-tab (not shown) may also be provided near the distal end of detachable portion 102 to facilitate removal of the detachable portion. Features such as frangible seam 112 and slot 110 can also serve as markers to ensure proper loading of the compressible implant.

Figure 3:
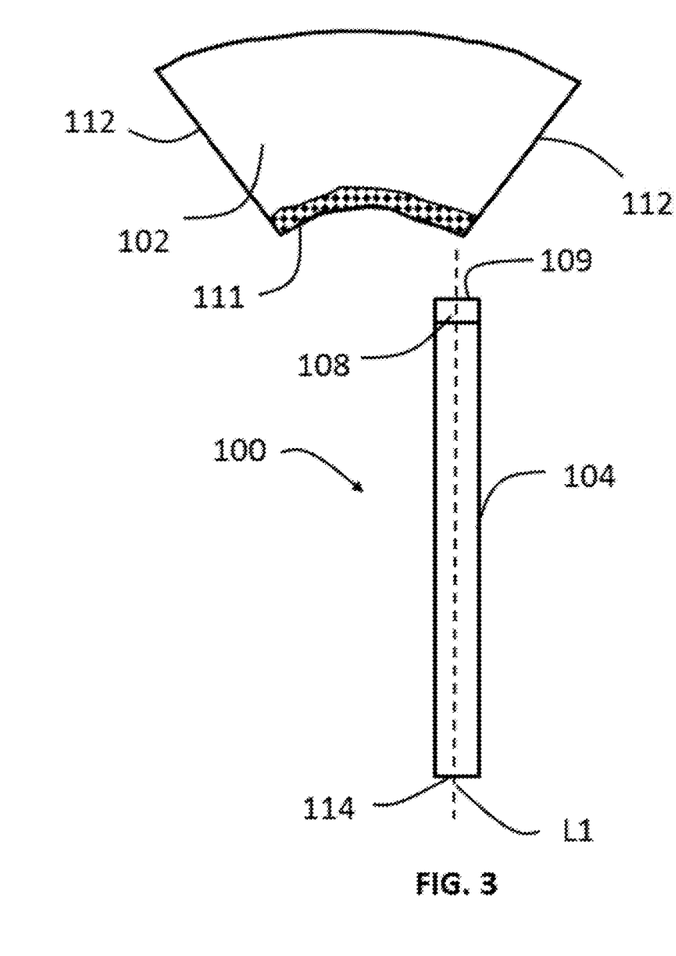
FIG. 3 is a front view of the distal portion of the delivery system of FIG. 1 with the detachable portion detached therefrom.

Referring now to FIG. 3, delivery system 100 is shown with detachable portion 102 detached from sheath 104. A frangible connection 111 located at the proximal end of detachable portion 102 may enable the detachable portion to be separated from sheath 104. Frangible connection 111 may be used in conjunction with the other frangible features described above to conveniently detach and remove detachable portion 102 from delivery system 100. Frangible connection 111 may be an adhesive layer that can be peeled away, a weakened section of detachable portion 102 that can be broken, or a breakable web, perforated layer or other features that may be readily separated from band 108 by twisting and/or pulling detachable portion 102. For example, an operator may conveniently grasp the pull-tab of slot 110 and pull along direction 115 to tear seam 112 from second opening 107 to first opening 106 as best shown in FIGS. 2 and 3. Further pulling of the pull-tab in direction 115 will separate detachable portion 102 from band 108 via frangible connection 111 based on the type of frangible connection 111 being utilized. Alternatively, a separate pull-tab or other easy grasp feature may be integrated directly on frangible connection 111 to enable the separation of detachable portion 102 from band 108. For example, detachable portion 102 may be joined to band 108 by a removable strip, as in a plastic milk container. By pulling a tab at the free end of the strip around the circumference of sheath 104 to break weakened edges along both sides of the strip, the strip may be removed, thereby leaving detachable portion 102 free for removal from the sheath. In other embodiments, a perforated or otherwise weakened seam may be broken by pulling a wire, string, suture or other filament buried below the seam and through the seam to separate detachable portion 102 from band 108. Frangible connection 111 provides a clean break from the band 108 of sheath 104, leaving behind a flat and smooth distal surface 109 without any rough edges or sharp corners. Rather than using frangible features, detachable portion 102 and sheath 104 may include complementary fasteners that enable a user to remove the detachable portion from the sheath, and to then reattach it if desired. For example, detachable portion 102 and sheath 104 may have interlocking or snap-fitting components that can be disengaged to detach the detachable portion from the sheath and engaged to attach or reattach the detachable portion to the sheath.

Figure 4:
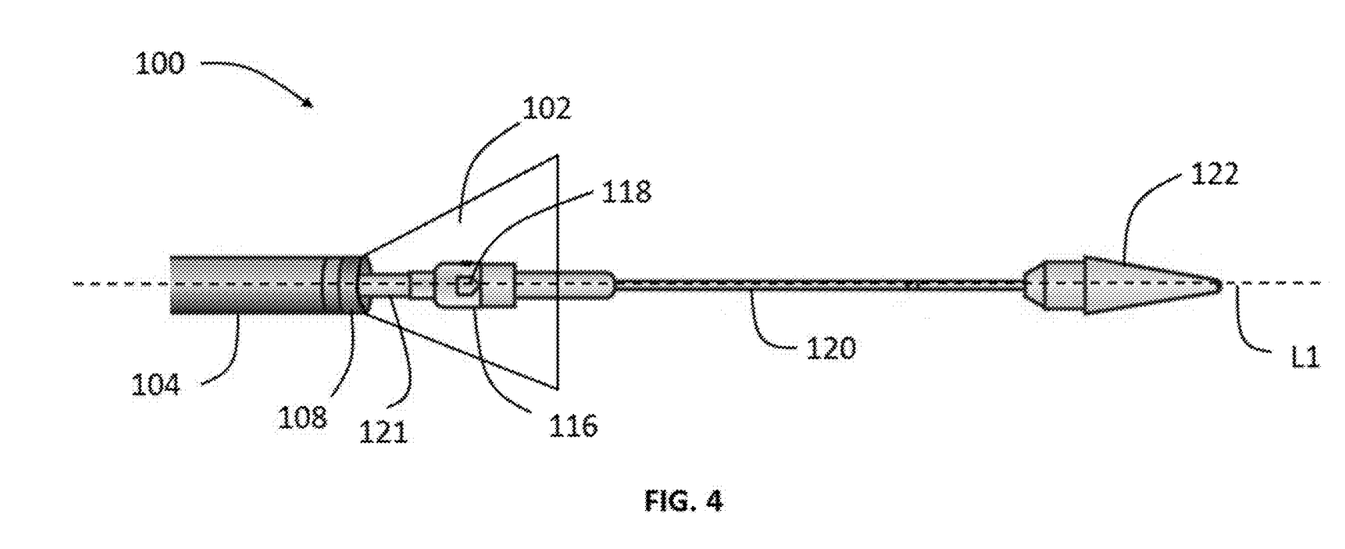
FIG. 4 is a front view of the delivery system of FIG. 1 in an extended position.
Figure 5:
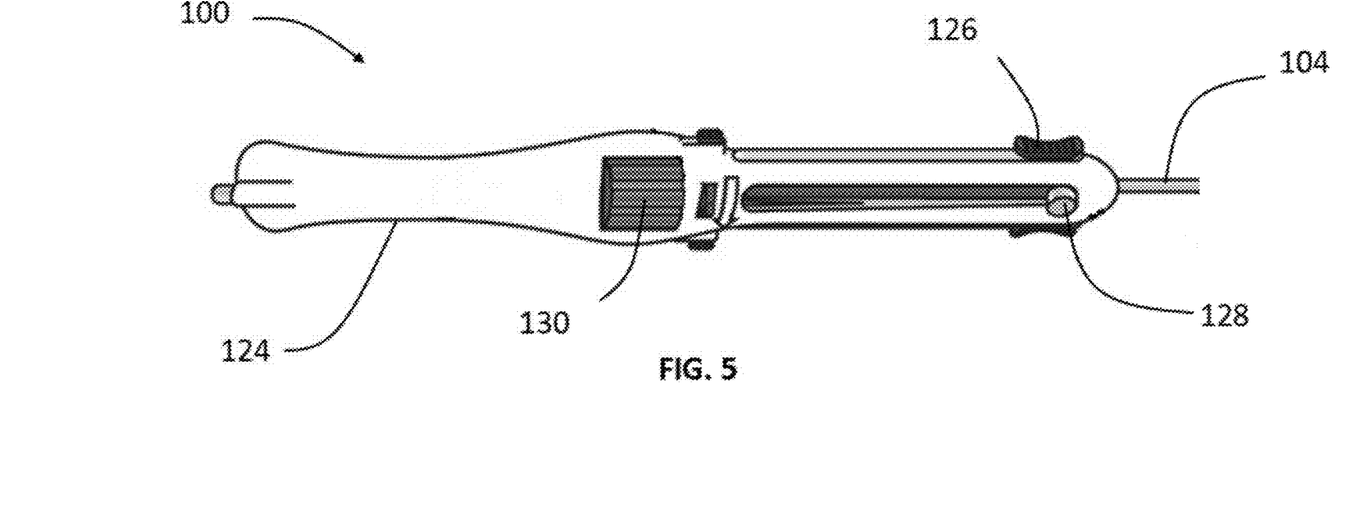
FIG. 5 is a front view of a handle of the delivery system of FIG. 1.

FIG. 4 shows delivery system 100 in an extended position, and FIG. 5 shows a handle 124 of the delivery system. A first shaft 120 extends distally away from sheath 104 along longitudinal axis L1, terminating at a distal tip 122. A retaining element 116 linked to shaft 120 and having retaining features such as recesses 118 is positioned distally of sheath 104 and in the interior of detachable portion 102. The proximal end of retaining element 116 is attached to a second larger shaft 121. Retaining element 116 is configured to connect to and secure a compressible implant during advancement to a target site, and to enable the compressible implant to be retracted into sheath 104 for repositioning or removal from the patient. The proximal end of shaft 121 is connected to another system or mechanism, such as handle 124. Handle 124 includes sliding controls 126 and deployment controls 130 to precisely control extension and retraction of shafts 102 and 121 relative to sheath 104. Flush ports 128 are also provided on handle 124 for de-airing delivery system 100. Mechanisms for extending components from and retracting components into sheath 104 are described in International Patent Application Publication No. WO/2009/091509, the entire contents of which are hereby incorporated herein by reference.

Figure 6:
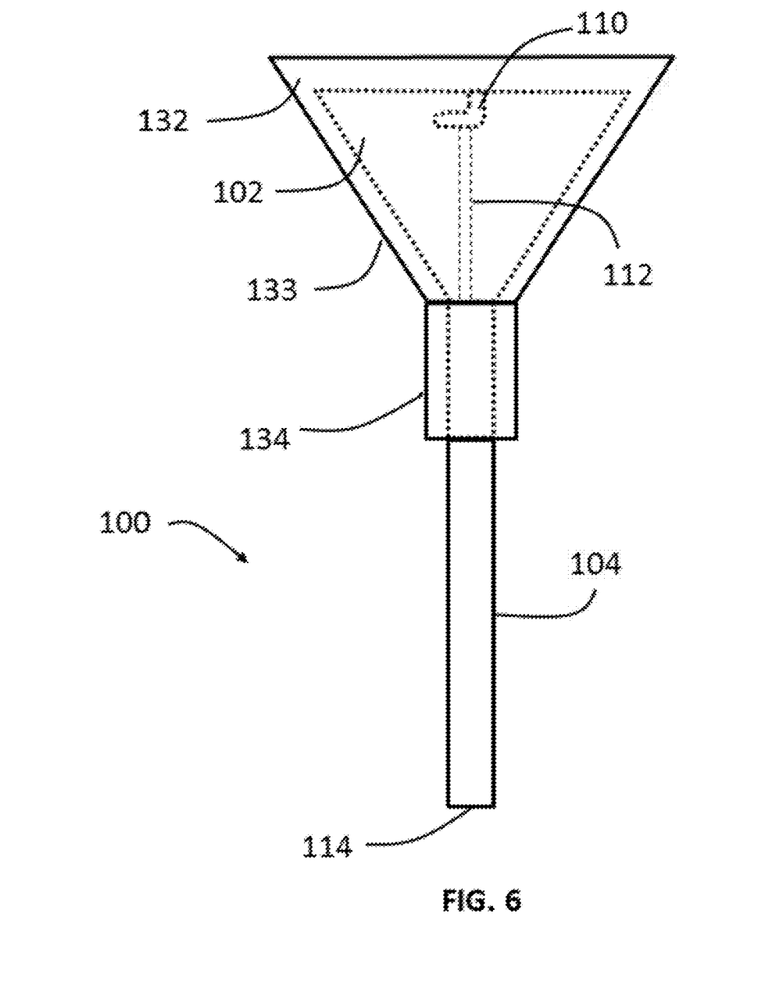
FIG. 6 is a front view of the distal portion of the delivery system of FIG. 1 with a support structure according to another embodiment of the present invention.

Referring now to FIG. 6, there is shown a support structure 132 placed over delivery system 100 according to another embodiment of the present invention. Support structure 132 consists of a generally cone-shaped distal end 133 and a cylindrical proximal end 134. When support structure 132 is placed over delivery system 100, cone-shaped distal end 133 is configured to cover and provide external support to detachable portion 102, whereas proximal end 134 covers the distal end of sheath 104. Support structure 132 can include a slit (not shown) extending in a distal-proximal direction along its entire length to enable a user to conveniently place the support structure over or remove the support structure from delivery system 100. L-shaped slot 110 may be configured to engage with a complementary attachment feature on support structure 132 to secure detachable portion 102 to the support structure. Support structure 132 is particularly useful for detachable portions 102 made of a flexible material that enables the compressible implant to collapse as it progresses through the detachable portion.

Detachable portion 102 can be integrated into the delivery system 100 during fabrication of the delivery system, or the detachable portion can be attached to the delivery system by interlocking features, snap fitting mechanisms, adhesives or other features. Alternatively, the detachable portion may have a tail extending distally from the first opening that may be slightly larger than diameter D1 to enable an interference fit between the detachable portion and the delivery system. This will allow an operator to compress the tail and insert it into the sheath to secure detachable portion to the delivery system.

Figure 7:
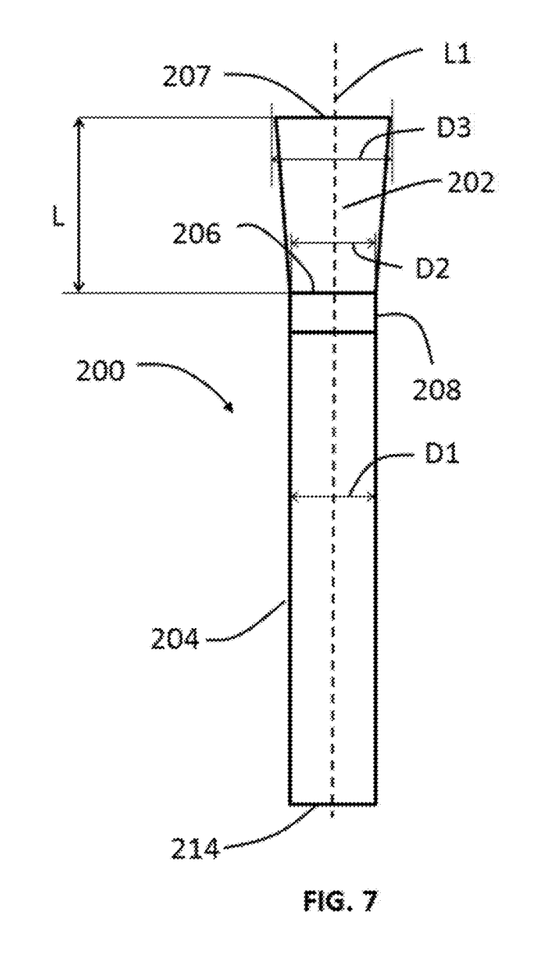
FIG. 7 is a front view of the distal portion of a delivery system with a detachable portion according to another embodiment of the present invention.

FIG. 7 shows a delivery system 200 according to another embodiment of the present invention. Delivery system 200 is similar to delivery system 100, and therefore like elements are referred to with similar numerals within the 200-series of numbers. For instance, delivery system 200 includes a sheath 204 having a band 208 and a detachable portion 202. However, the diameter D3 of second opening 207 is only slightly larger than the diameter D2 of first opening 206. Consequently, there is less compression of the collapsible implant as it passes from second opening 207 to first opening 206 in this embodiment. This feature may be desirable when only marginal compression of the collapsible implant is necessary for loading into a delivery system. Other embodiments can have various dimensions for D3 and L to control the rate of compression imparted to the compressible implant. For example, increasing the length L of detachable portion 202 while keeping diameters D2 and D3 constant will result in a lower rate of compression, whereas decreasing length L can increase the rate of compression imparted to a collapsible implant as it passes through the detachable portion when dimensions D3 and D2 are constant. Alternatively, diameter D3 may be equal to diameter D2, whereby no compression is imparted to the compressible implant. In this instance, detachable portion 202 may serve as a sacrificial portion to protect the distal end of sheath 204. That is, if detachable portion 202 is damaged during loading of the compressible implant, the detachable portion may be removed, thereby preserving a pristine, undamaged distal end of the sheath for insertion into and advancement through the vasculature of the patient.

Figure 8:
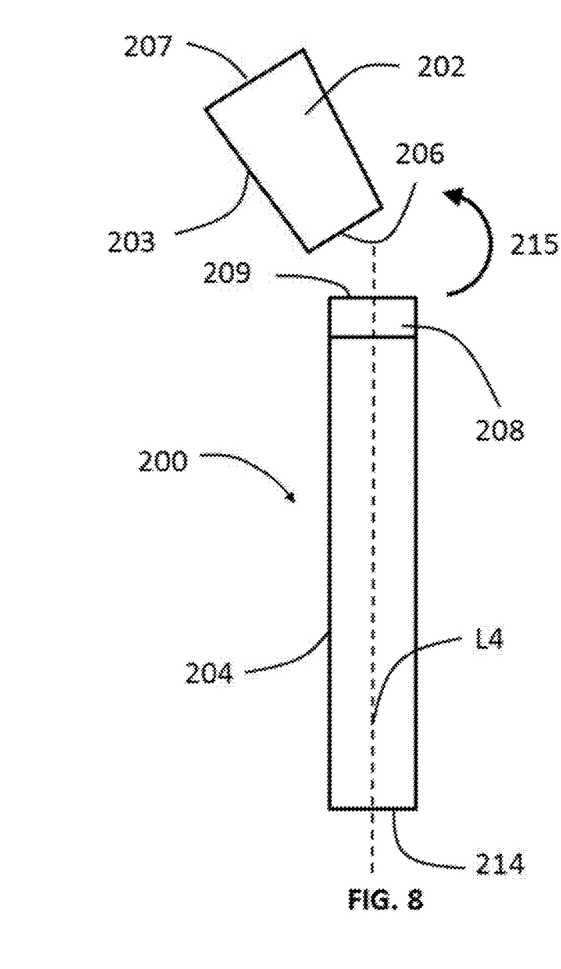
FIG. 8 is front view of the distal portion of the delivery system of FIG. 7 with the detachable portion detached therefrom.

Detachable portion 202 does not include any frangible features in this embodiment. Instead, a cutting instrument can be used to separate detachable portion 202 from delivery system 200 as best shown in FIG. 8. The cutting instrument may be a surgical blade or other specialized tool which enables detachable portion 202 to be cleanly separated from delivery system 200 to leave being a flat and smooth distal surface 209. Detachable portion 202 may be formed integrally with the band 208 of sheath 204, and may include various features to enable it to be conveniently detached therefrom. Detachable portion 202 may be creased, crimped, embossed, perforated, scored or otherwise weakened along a seam so that an operator may conveniently pull apart detachable portion 202 at the seam as more fully described above with reference to detachable portion 102.

While a continuous wall is shown extending between the first and second openings of detachable portions 102 and 202, other embodiments can have a plurality of struts, ribs, partial wall segments or any combination thereof, extending from the first opening toward the second opening in a direction substantially perpendicular to the openings instead of a continuous wall. Detachable portions 102 and 202 can be made of an elastic material that flexes during passage of the compressible implant to prevent any damage to the implant. The detachable portion can be made of the same material as the delivery system, such as polytetrafluoroethylene ("PTFE") or other similar materials. If the detachable portion is made of the same material as the delivery system, the detachable portion may be integrally fabricated as an extension of the delivery system.

Figure 9:
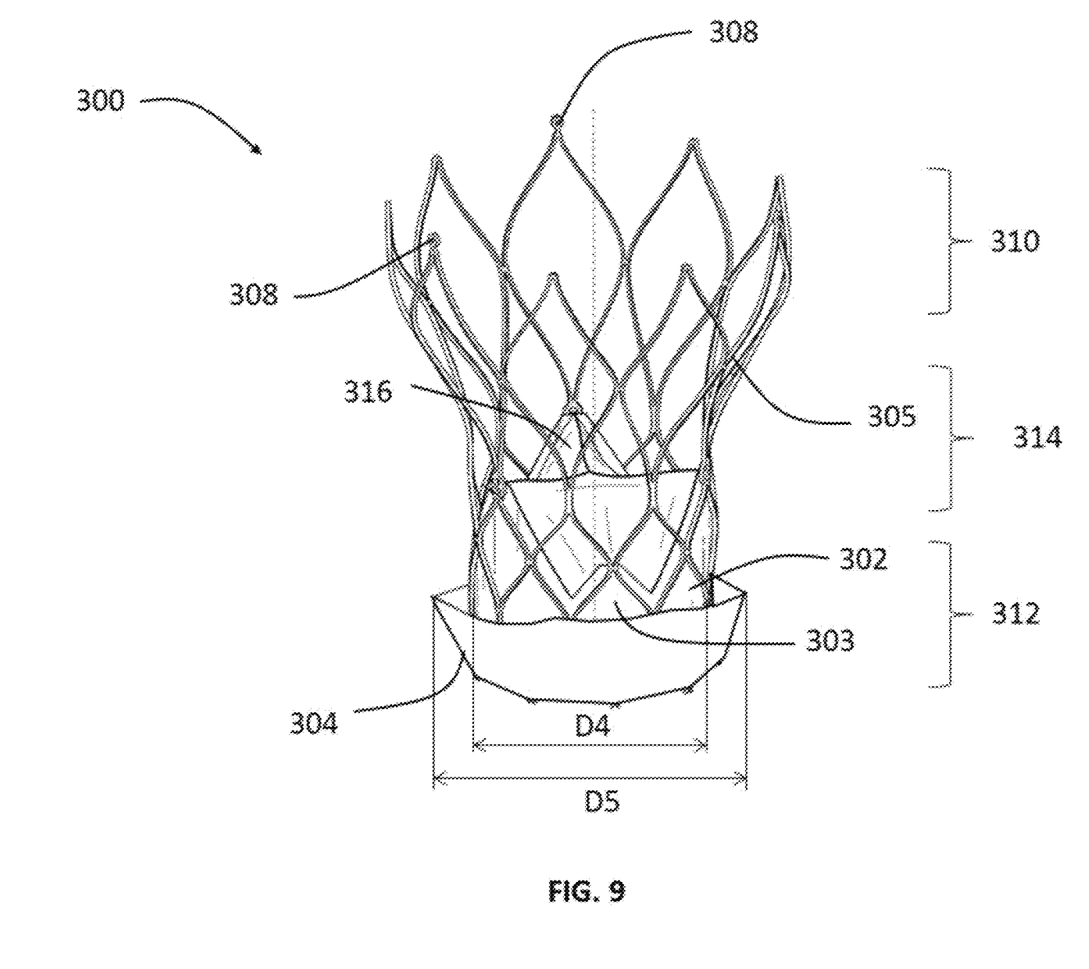
FIG. 9 is a front perspective view of a self-expanding prosthetic heart valve.

Referring to FIG. 9, there is shown an exemplary compressible heart valve 300 that can be loaded into a delivery system having one of the detachable portions of the present disclosure. While valve 300 is shown in an expanded condition in FIG. 9, valve 300 will compress to a collapsed condition for insertion into the delivery system. Valve 300 has a collapsible framework or stent 305, with a valve assembly 302 internally connected to the stent. Stent 305 can be formed from any suitable biocompatible material, such as nitinol, and can include an annulus section 312, an aortic section 310, and an intermediate section 314. Aortic section 310 may have a larger diameter than the diameter D4 of annulus section 312. Valve assembly 302 may include a plurality of leaflets 316, an inner cuff 303, and an outer cuff 304. Leaflets 316 and cuffs 303 and 304 may be formed from a biocompatible polymer, from bovine or porcine pericardial tissue, or from other appropriate biocompatible materials. Valve assembly 302 is connected to stent 305 generally within annulus section 312, but may extend into intermediate section 314. Valve 300 can include tabs or retaining members 308 at spaced positions around one or both ends of stent 305. Retaining members 308 are configured for engagement within the recesses 118 of retaining element 116 as described more fully above.

Figure 10:
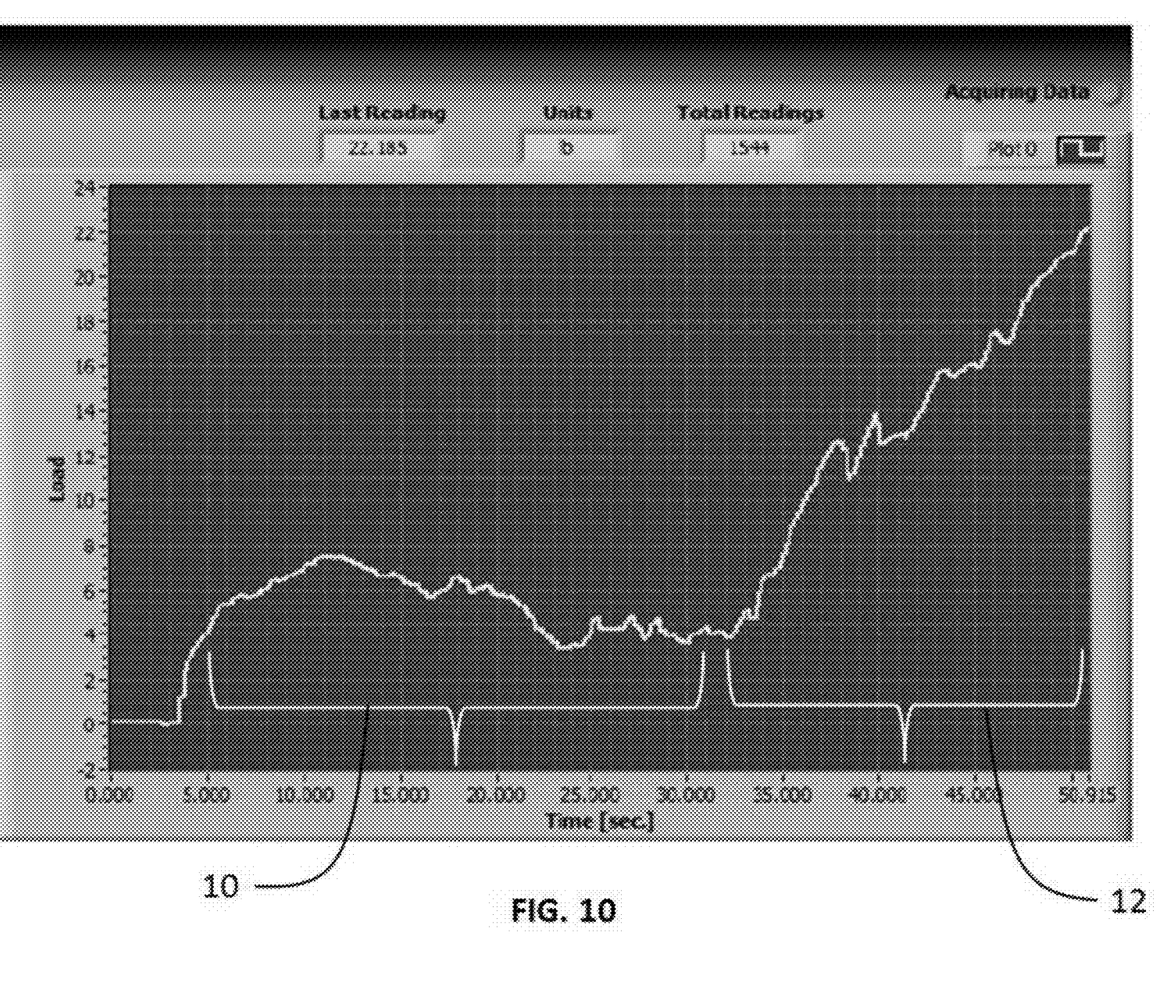
FIG. 10 is a graph plotting loading forces encountered during loading of the heart valve of FIG. 9 into a delivery system without a detachable portion.

Outer cuff 304 extends towards aortic section 310 radially outward of stent 305. As best seen in FIG. 9, outer cuff 304 has an external diameter D5 that is greater than the diameter D4 of annulus section 312 so that the outer cuff is spaced away from stent 305. Outer cuff 304 is designed to fill any gaps between the stent body and the native valve annulus after implantation to minimize or prevent paravalvular leakage. Loading valve 300 having outer cuff 304 into a delivery system without one of the detachable portions described herein may cause the outer cuff to get caught or entangled on the outside of the distal end of the delivery system sheath. This phenomenon is illustrated in FIG. 10, which shows a graph of the forces required to load valve 300 into a delivery system without a detachable portion. As best indicated by region 10, the loading forces are generally constant until outer cuff 304 contacts the distal end of the sheath of the delivery system. Region 12 depicts the spike in loading forces required to compress outer cuff 304 into the distal end of the delivery system sheath, particularly as the outer cuff gets caught on the distal end of the sheath. Consequently, increased effort may be required to load the heart valve into a delivery system without a detachable portion. Furthermore, this may result in excessive compression of the heart valve and/or damage to the delivery system.

Figure 11A:
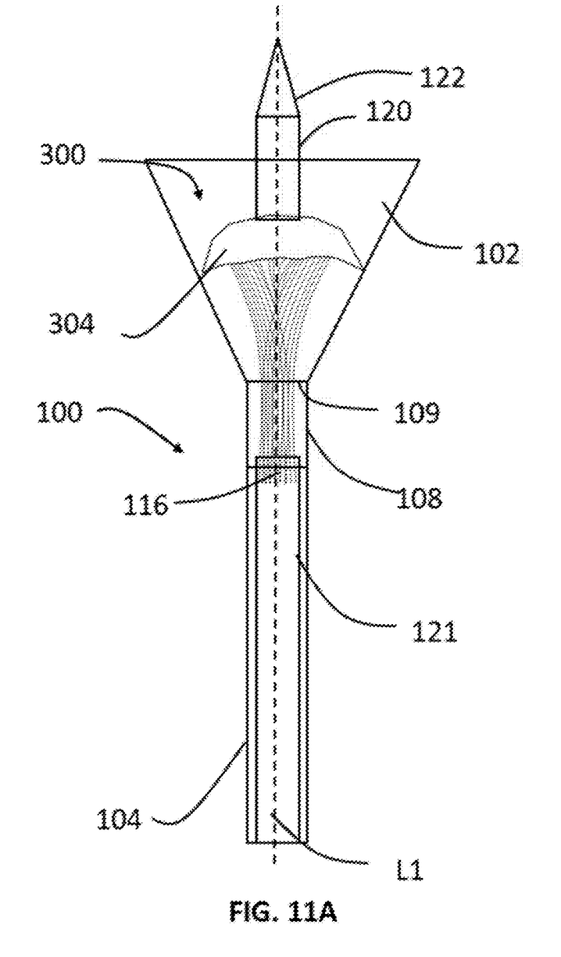
FIGS. 11A-11D are schematic front views showing steps for loading the heart valve of FIG. 9 into the delivery system of FIG. 1.
Figure 11B:
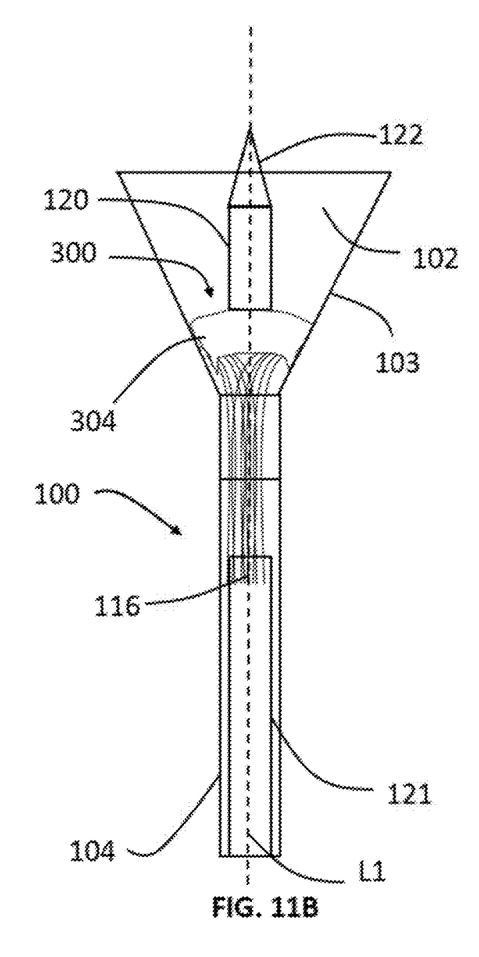
Figure 11C:
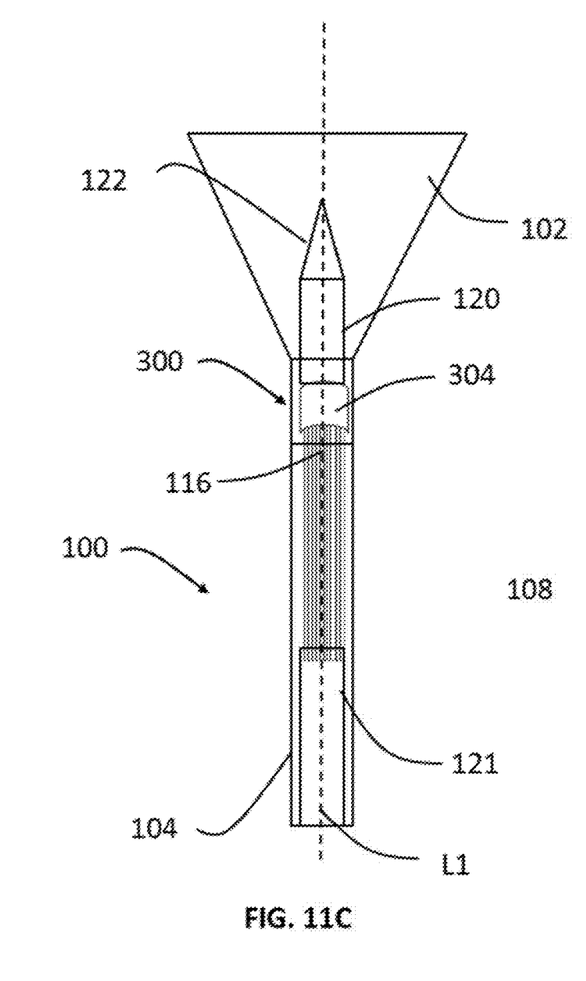
Figure 11D:
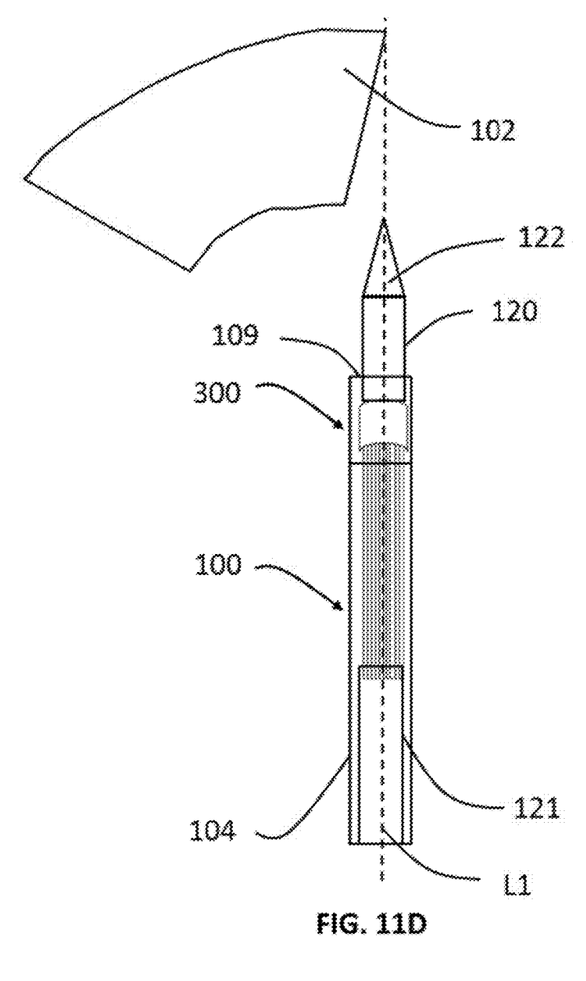

FIGS. 11A-11D show a method of loading valve 300 into delivery system 100 having detachable portion 102. Valve 300 can be secured to retainer 116 as described in U.S. Patent Application Publication No. 2017/0035570, the entire contents of which are hereby incorporated herein by reference. Subsequently, shaft 121 is retracted into sheath 104 as shown in FIG. 11A, gradually compressing valve 300 from aortic section 310 to intermediate section 314. Annulus section 312 and outer cuff 304 are in a fully or almost fully expanded condition at this stage. As shaft 121 is further retracted into sheath 104, outer cuff 304 contacts the wall 103 of detachable portion 102 and begins to compress as shown in FIG. 11B. Shaft 121 is retracted further into sheath 104, which causes wall 103 to further compress outer cuff 304 until the diameter D5 of the outer cuff is the same as the diameter D2 of first opening 106 and the internal diameter D1 of sheath 104. This allows the entire valve to slide into sheath 104 as shown in FIG. 11C. Detachable portion 102 can then be removed from sheath 104 by using the frangible features described above to leave behind a flat smooth distal surface 109 at the end of the sheath, as shown in FIG. 11D. Alternatively, support structure 132 can be placed around detachable portion 102 and sheath 104 prior to retracting shaft 121 to provide additional rigidity as valve 300 is compressed and guided into delivery system 100.

While heart valve 300 is shown as a collapsible implant suitable for loading into the delivery system of the present disclosure, as will be readily apparent from the above description pertaining to other embodiments, the present disclosure is not limited to any particular type of collapsible implant. Rather, it is contemplated that certain features of the present disclosure can be implemented for different types of collapsible implants.

To summarize the foregoing, a first aspect of the disclosure describes a delivery system for a collapsible heart valve, including a delivery capsule having a longitudinal axis and a distal opening to receive a collapsible heart valve, the distal opening having an internal diameter; and a detachable portion having a first open end with a first diameter, a second open end with a second diameter, and a guide wall, the guide wall defining an open space adapted to receive the valve, the first open end being attached to the distal opening of the delivery capsule and the first diameter being substantially the same as the internal diameter of the distal opening of the delivery capsule such that an inner surface of the guide wall and the distal opening form a continuous surface extending from the detachable portion and into the delivery capsule, wherein the detachable portion is detachable from the delivery capsule; and/or the second open end may have a second diameter greater than the first diameter and the guide wall may decrease in diameter from the second open end to the first open end; and/or the first diameter may be less than a diameter of the collapsible heart valve in an uncompressed state such that the heart valve may be compressed as it passes from the second open end to the first open end; and/or the guide wall may include one or more walls; and/or the guide wall may include one or more struts; and/or the detachable portion may be attached to the delivery capsule by a frangible member such that the detachable portion can be detached from the delivery capsule by breaking the frangible member; and/or the frangible member may include a breakaway band such that the detachable portion can be detached from the delivery capsule by breaking the breakaway band; and/or the frangible member may be formed by a procedure selected from the group consisting of creasing, crimping, embossing, perforating and scoring the detachable portion; and/or the frangible member may be a marker to position and guide the collapsible heart valve; and/or the detachable portion may be made of a flexible material; and/or the flexible material may be polytetrafluoroethylene; and/or the delivery system may further comprise a support structure configured to be placed around the delivery capsule and the detachable portion, a distal portion of the support structure may be similar in shape to the guide wall; and/or the detachable portion may be connected to the delivery capsule by releasable connectors that enable the detachable portion to be detached from and reattached to the delivery capsule.

Another aspect of the disclosure describes a method of loading a collapsible heart valve into a delivery system, the method including providing a delivery system having a retainable, a delivery capsule with a distal opening, the distal opening having an internal diameter, a detachable portion having a first open end with a first diameter, a second open end with a second diameter greater than the first diameter, and a tapered wall decreasing in diameter from the second open end to the first open end, the tapered wall defining an open space, the first open end being integrally connected to the distal opening of the delivery capsule and the first diameter being substantially the same as the internal diameter of the distal opening of the delivery capsule such that an inner surface of the tapered wall and the distal opening form a continuous surface extending from the detachable portion and into the delivery capsule; attaching the heart valve to the retaining element; and loading the heart valve into the delivery system by retracting the retaining element proximally such that the tapered wall collapses the heart valve as the heart valve moves from the second open end to the first open end and into the delivery capsule; and/or the method may further comprise removing the detachable portion from the delivery capsule such that the distal opening has a smooth distal surface; and/or the removing step may include breaking a frangible member between the detachable portion and the delivery capsule; and/or the removing step may include peeling away a band between the detachable portion and the delivery capsule; and/or the removing step may include cutting the detachable portion from the delivery capsule; and/or the loading step may include placing a support structure around the delivery capsule and the detachable portion prior to retracting the retaining element proximally such that the support structure may guide the heart valve as the heart valve moves from the second open end to the first open end and into the delivery capsule.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A delivery system for a collapsible heart valve, comprising:
    a delivery capsule having a longitudinal axis and a distal opening to receive a collapsible heart valve, the distal opening having an internal diameter; and
    a detachable portion having a first open end with a first diameter, a second open end with a second diameter, and a guide wall, the guide wall defining an open space adapted to receive the collapsible heart valve, the first open end being attached to the distal opening of the delivery capsule and the first diameter being substantially the same as the internal diameter of the distal opening of the delivery capsule such that an inner surface of the guide wall and the distal opening form a continuous surface extending from the detachable portion and into the delivery capsule, the detachable portion including a first frangible member extending from the first open end to the second open end and a second frangible member extending around the first open end, the first frangible member contacting the second frangible member,
    wherein the detachable portion is detachable from the delivery capsule.

2. The delivery system of claim 1, wherein the second diameter is greater than the first diameter, and the guide wall decreases in diameter from the second open end to the first open end.

3. The delivery system of claim 2, where the first diameter is less than a diameter of the collapsible heart valve in an uncompressed state such that the collapsible heart valve is compressed as it passes from the second open end to the first open end.

4. The delivery system of claim 1, wherein the guide wall includes one or more walls.

5. The delivery system of claim 1, wherein the guide wall includes one or more struts.

6. The delivery system of claim 1, wherein the detachable portion can be detached from the delivery capsule by breaking the first frangible member from the second open end to the first open end and subsequently breaking the second frangible members around the first open end.

7. The delivery system of claim 6, wherein the second frangible member includes a breakaway band such that the detachable portion can be detached from the delivery capsule by breaking the breakaway band.

8. The delivery system of claim 6, wherein the second frangible member is formed by a procedure selected from the group consisting of creasing, crimping, embossing, perforating and scoring the detachable portion.

9. The delivery system of claim 6, wherein the second frangible member is a marker to position and guide the collapsible heart valve.

10. The delivery system of claim 1, wherein the detachable portion is made of a flexible material.

11. The delivery system of claim 10, wherein the flexible material is polytetrafluoroethylene.

12. The delivery system of claim 1, further comprising a support structure configured to be placed around the delivery capsule and the detachable portion, a distal portion of the support structure being similar in shape to the guide wall.

13. The delivery system of claim 1, wherein the first frangible member includes a tab at the second open end, the tab configured to allow an operator to break the first frangible member from the second open end to the first open end.

* * * * *